United States Patent

Bahrmann

Patent Number: 5,817,884
Date of Patent: Oct. 6, 1998

[54] PROCESS FOR PREPARING ALDEHYDES

[75] Inventor: Helmut Bahrmann, Hamminkeln, Germany

[73] Assignee: Hoechst Aktiengesellschaft, Germany

[21] Appl. No.: 856,276

[22] Filed: May 14, 1997

[30] Foreign Application Priority Data

May 15, 1996 [DE] Germany .......... 196 19 527.6
Aug. 13, 1996 [DE] Germany .......... 196 32 602.8

[51] Int. Cl.$^6$ .......... C07C 45/50
[52] U.S. Cl. .......... 568/454; 568/451; 210/651; 210/644
[58] Field of Search .......... 568/451, 454; 210/651, 644

[56] References Cited

FOREIGN PATENT DOCUMENTS 0374615  6/1990  European Pat. Off. .
0588225  3/1994  European Pat. Off. .

Primary Examiner—Gary Geist
Assistant Examiner—Sreeni Padmanabhan
Attorney, Agent, or Firm—Bierman, Muserlian and Lucas

[57] ABSTRACT

A process for preparing aldehydes by hydroformylation of olefinically unsaturated compounds with hydrogen and carbon monoxide in a homogeneous phase in the presence of a catalyst system comprising organometallic complex compounds and ligands of these complex compounds in molar excess, and separating off the catalyst system from the hydroformylation reaction mixture by pressure filtration on a semipermeable membrane of an aromatic polyamide, the mass molar ratio of the ligands present in excess to the aldehydes prepared is 9–30, preferably 10–25, in particular 10–15, with the ligands present in excess not being alkylammonium or arylammonium salts of sulfonated, carboxylated or phosphonated aromatic diphosphines which by maintaining the molar mass ratio, not only are high activation and selectivity values obtained in the hydroformylation itself, but also excellent retention values for the catalyst system are obtained in the membrane filtration step.

18 Claims, No Drawings

PROCESS FOR PREPARING ALDEHYDES

FIELD OF THE INVENTION

The invention relates to a process for preparing aldehydes by reacting olefinically unsaturated compounds with hydrogen and carbon monoxide in a homogeneous phase and in the presence of a catalyst system comprising organometallic complex compounds and ligands of these complex compounds in molar excess, and separating the catalyst system from the reaction product by pressure filtration on a semipermeable membrane of an aromatic polyamide.

STATE OP THE ART

The hydroformylation of olefins, carried out industrially to a great extent, is increasingly being performed in the presence of catalyst systems based on rhodium complex compounds which comprise tertiary phosphines or phosphites as ligands. Since the ligands are generally present in excess, the catalyst system comprises organometallic complex compound and additional pure ligand. In accordance with the solubility of these catalyst systems in organic media, the hydroformylation is performed in a homogeneous phase. To separate off the reaction product and recover the catalyst system homogeneously dissolved in the reaction product, the reaction product is generally distilled off from the reaction mixture. However, owing to the thermal sensitivity of the aldehydes formed, this is only possible in the hydroformylation of lower olefins having up to about 8 carbon atoms in the molecule.

In the hydroformylation of long-chain olefins or olefinic compounds having functional groups, thermally sensitive products, or products having a high boiling point, are formed, which can no longer be satisfactorily separated off from the catalyst by distillation. The thermal stress of the distillation material leads, owing to thick oil formation, to considerable losses of valuable product and, owing to decomposition of the complex compounds, to losses of catalyst. This critically decreases the economic attractiveness of the process.

To avoid separating off the catalyst system in a thermal manner, various processes have been developed. EP-A-0 374 615 discloses that organometallic complex compounds may be separated off and recovered undamaged, i.e. without degradation of the catalytically active metal compound, from organic solvents using selective semipermeable polyaramid separation membranes. Either a pressure difference (pressure filtration) or a concentration difference (dialysis) can serve as the motive force for the separation process in this case. The process is particularly suitable for separating off organometallic complex compounds and/or metal carbonyls having phosphorus(III) compounds as ligands from organic solutions in which they have previously been used as homogeneous catalysts.

Rhodium complex compounds which can be used for the homogeneous hydroformylation of olefins which are mentioned in EP-A-0 374 615 are $HRhCO[P(C_6H_5)_3]_3$, $RhCl[P(C_6H_5)_3]_3$ and those compounds which contain, as ligands, alkylammonium or arylammonium salts of sulfonated or carboxylated triarylphosphines of the formula

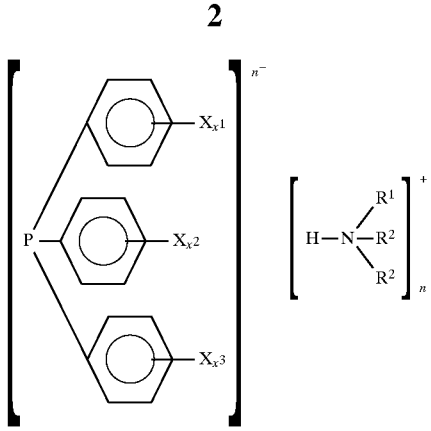

where X is sulfonate ($SO_3^-$) or carboxylate ($COO^-$), $x^1$, $x^2$ and $x^3$ are 0 or 1, $R^1$ and $R^2$ are individually alkyl of 4 to 12 carbon atoms, aryl of 6 to 12 carbon atoms or cycloalkyl of 6 to 12 carbon atoms and $R^1$ can additionally also be hydrogen.

In the two-stage membrane separation of a catalyst system comprising a rhodium and the triisooctylammonium salt of tris(m-sulfophenyl)phosphine from the crude product of the dicyclopentadiene hydroformylation, according to EP-A-0 374 615, 99.5% of rhodium and 94.4% of the phosphorus (III) compound are retained. 5.6% of the phosphorus(III) compound thus remains in the organic hydroformylation product and can be removed therefrom only by complex measures, such as a complicated distillation with relatively large product losses. The flow rate in the final steady state of membrane filtration is only 5 or 10 $1/m^2$ h in the first or second membrane filtration stage, respectively.

OBJECTS OF THE INVENTION

An object of the invention is to provide a process for the hydroformylation of olefinically unsaturated compounds in a homogeneous phase which gives high activities and selectivities and simultaneously enables improved separation of the entire catalyst system.

This and other objects and advantages of the invention will become obvious from the following detailed description.

THE INVENTION

The novel process of the invention for preparing aldehydes comprises hydroformylating olefinically unsaturated compounds with hydrogen and carbon monoxide in a homogeneous phase in the presence of a catalyst system comprising organometallic complex compounds and ligands of these complex compounds in molar excess, and separating off the catalyst system from the hydroformylation reaction mixture by pressure filtration on a semipermeable membrane of an aromatic polyamide, in which the molar mass ratio of the ligands present in excess to the aldehydes prepared is 9–30 with the ligands present in excess not being alkylammonium or arylammonium salts of sulfonated, carboxylated or phosphonated aromatic diphosphines. Preferably the molar mass is 10 to 25 and more preferably 10 to 15.

By the novel process, it is possible to recover, virtually without loss, the organometallic complex compounds and the ligands of these complexes present in excess unchanged, i.e. without their being decomposed or experiencing another conversion.

Organometallic complex compounds in the context of the invention are intended to mean compounds in which carbon atoms of organic groups are bound to metal atoms. The metals also include the so-called semimetals such as boron and silicon. According to the invention, the compounds which are soluble in an organic solvent in which the bond between metal and carbon is made via nitrogen, oxygen or sulfur are also termed organometallic complex compounds.

The metal of the organometallic compounds is preferably an element of groups IVA, VA, VIA, VIIA, VIIIA or IB of the Periodic Table of the Elements and, preferred are manganese, iron, cobalt, nickel, palladium, platinum, ruthenium, rhodium and iridium.

The organometallic complex compounds contain, in addition to the metals, ligands such as CO, hydrogen, amines, phosphines, phosphites, acetate, benzonitrile, acetylacetonates, dimethylglyoximes, π-olefins such as 1,5-cyclooctadiene, or π-aromatics such as cyclopentadienyl.

The ligands present in excess in the catalyst system are preferably monodentate ligands, with the molar ratio of monodentate ligands to organometallic complex compound in the hydroformylation being at least 50, preferably 60 to 120, and, more preferably, 80 to 100.

Particularly suitable monodentate ligands are aromatic phosphines and, in this case, preferred are alkylammonium and/or arylammonium salts of sulfonated or carboxylated triarylphosphines. Most preferably, the distearylammonium salt of triphenylphosphine-trisulfonate is used.

In addition, sulfonated pyridines, quinolines, 2,2'-bipyridines, porphyrins and pyridylphosphines, quinine, glyoxime, sulfonated phosphites and alkyl- and aryl-substituted acetylacetonates, salicylates and mandelates have proved to be useful as ligands present in excess.

The olefin is reacted with carbon monoxide and hydrogen at a temperature of 100° to 140° C., preferably 120° to 130° C. and at a pressure of 0.5 to 27 MPa, preferably 20 to 25 MPa. The composition of the synthesis gas, i.e. the volumetric ratio of carbon monoxide and hydrogen, can extend over broad ranges and can be varied, e.g., between 1:10 to 10:1. Generally, gas mixtures are used in which the volumetric ratio of carbon monoxide to hydrogen is about 1:1 or deviates only slightly from this value.

In the process of the invention, olefinically unsaturated compounds of 2 to 30 carbon atoms which can have one or more double bonds are reacted. Suitable substances are substituted or unsubstituted alkenes of 6 to 30 carbon atoms, substituted or unsubstituted dienes of 4 to 10 carbon atoms, substituted or unsubstituted cycloalkenes or dicycloalkenes of 5 to 12 carbon atoms in the ring system, esters of an unsaturated carboxylic acid of 3 to 20 carbon atoms and of an aliphatic alcohol of 1 to 18 carbon atoms, esters of a saturated carboxylic acid of 2 to 20 carbon atoms and of an unsaturated alcohol of 2 to 18 carbon atoms, unsaturated alcohols or ethers of 3 to 20 carbon atoms or araliphatic olefins of 8 to 20 carbon atoms.

The substituted or unsubstituted alkenes of 6 to 30 carbon atoms can be linear or branched alkenes having a terminal or internal position of the double bond. Preference is given to linear olefins of 6 to 18 carbon atoms such as n-hex-1-ene, n-hept-1-ene, n-oct-1-ene, n-non-1-ene, n-dec-1-ene, n-undec-1-ene, n-dodec-1-ene, n-octadec-1-ene and acyclic terpenes. Suitable substances also are branched alkenes such as diisobutylene (2,4,4-trimethylpent-1-ene), tripropylene, tetrapropylene and dimersol (dibutylene).

Preferred examples of unsubstituted dienes of 4 to 10 carbon atoms are 1,3-butadiene, 1,5-hexadiene and 1,9-decadiene.

Examples of substituted and unsubstituted cycloalkenes or dicycloalkenes of 5 to 12 carbon atoms in the ring system are cyclohexene, cyclooctene, cyclooctadiene, dicyclopentadiene and cyclic terpenes such as limonene, pinene, camphorene and bisabolene. An example of araliphatic olefins of 8 to 20 carbon atoms is styrene.

Examples of esters of an unsaturated carboxylic acid of 3 to 20 carbon atoms and an aliphatic alcohol of 1 to 18 carbon atoms are acrylic esters and methacrylic esters of 1–18 carbon atoms in the alcohol component.

The esters of a saturated carboxylic acid of 2 to 20 carbon atoms and an unsaturated alcohol of 2 to 18 carbon atoms include vinyl esters and allyl esters of 2–20 carbon atoms in the carboxylic acid component, such as vinyl acetate. The unsaturated alcohols and ethers include, for example, allyl alcohols and vinyl ethers.

Optionally, the process of the invention is carried out in the presence of an organic solvent which is inert under the hydroformylation conditions and, in addition, does not attack the membrane in the membrane filtration stage. Suitable solvents are aromatic hydrocarbons such as toluene, ortho-xylene, meta-xylene, para-xylene, mixtures of isomeric xylenes, ethylbenzene, mesitylene, mixtures of these compounds, or aliphatic hydrocarbons. However, more polar solvents such as acetophenone, tetrahydrofuran, sulfinol, glycols or polyglycols, can also be used. However, the hydroformylation reaction can also be carried out without addition of an organic solvent with the olefinic starting compound and the hydroformylation product formed acting as the solvent in this case. However, on account of the usually higher viscosity of a reaction mixture of this type, only relatively low flow rates are then generally achieved in the membrane filtration.

The catalyst system is formed from the metal or a metal compound and the ligands either in a step upstream of the hydroformylation, so-called preforming, or else, particularly in the case of the continuous procedure, in situ during the hydroformylation reaction. Both variants are described in the German patent application Ser. No. 196 19 527.6.

The aldehydes are prepared by reacting the reaction partners present in liquid and gaseous phases in conventional reactors, and can be prepared either continuously or else batchwise.

After the hydroformylation is completed, the reaction mixture is generally cooled, freed from gaseous constituents by expansion and blanketed with an inert gas such as nitrogen or with a synthesis gas mixture of CO and $H_2$. The mixture is then separated by means of membrane filtration. However, the reaction mixture can also be fed to the membrane filtration without cooling.

In the hydroformylation reaction mixture used for the membrane filtration, the concentration of the ligand of the organometallic complex compounds present in excess is 2.5 to 25, preferably 5 to 15, % by weight, based on the reaction mixture used for the membrane filtration.

The concentration of the organometallic complex compounds in the hydroformylation reaction mixture used for the membrane filtration is 2 to 400 ppm by weight, preferably 10 to 300 ppm by weight, more preferably 50 to 150 ppm by weight, based on the reaction mixture used for the membrane filtration.

The membrane filtration is performed on a polyaramid membrane under a pressure of 0.1 to 15, preferably 0.5 to 5, more preferably 1 to 2, MPa.

The membrane filtration can be carried out in a single stage or in multiple stages and preferably it is carried out in multiple stages, i.e. in two stages. It can be carried out either using parallel or series-connected separation stages. Preference is given to connection in series, in which the retentate is separated off in each stage and the permeate solution is passed to the next separation stage. A series connection in this manner permits a particularly effective utilization of the existing system pressure, i.e. the operating pressure in the preceding process step.

Particularly high separation efficiencies are achieved if the total amount of retentate is 8 to 90, preferably 10 to 70, more preferably 20 to 40, % based on the reaction mixture used, and the concentration of the separated ligands in the membrane filtration retentate is at least three times as high as in the hydroformylation reaction mixture used for the membrane filtration.

In the two-stage membrane filtration, it has, further, proved to be useful that the ratio of the amount of retentate of the 1st filtration stage to the amount of retentate of the 2nd filtration stage is about 1:1. A further increase in the separation efficiency of the membrane when the above-described process variant is used is achieved by increasing the overflow of the membrane using the circulation pump. The linear flow velocity over the membrane is usually in the range of 0.1 to 10 m/sec, preferably 0.5 to 2.5 m/sec.

The separation stage retentates containing the catalyst system can be combined and recycled back to the hydroformylation, optionally with supplementary addition of the metal and/or the organometallic complex compounds and the ligands of the complex compounds. These supplementary amounts can, in the case of a two-stage membrane filtration procedure, also even be added to the permeate of the 1st stage prior to its being fed to the 2nd membrane filtration.

In this manner, an improved separation result is achieved and multiple reuse of the catalyst system in the hydroformylation is enabled, without significant losses with regard to activity and selectivity of the catalyst system occurring.

If the process of the invention is carried out in the presence of a solvent, a particularly high total efficiency both of the hydroformylation step and of the membrane separation step can be achieved if the hydroformylation stage is operated with little solvent to achieve the highest possible conversion rate, but the membrane stage is operated with much solvent to decrease the viscosity. In the hydroformylation stage, a solvent content of 5 to 25% by weight, preferably 7 to 13% by weight, based on the total solvent-diluted reaction mixture, has proved to be useful. In contrast, in the membrane filtration step, 30 to 70% by weight, preferably 40 to 60% by weight, of solvent, based on the total solvent-diluted reaction mixture, is preferred.

This higher solvent content in the reaction mixture used for the membrane filtration is achieved by separating off the organic solvent from the combined permeates of the separation stages by distillation and recycling it upstream of the membrane filtration. There, it is added back to the hydroformylation reaction mixture to be separated. This attains an appropriate dilution which serves to achieve high flow rates.

The membranes used in the invention consist of an aromatic polyamide, also termed polyaramid. The polyaramids are obtained by polycondensation from aromatic dicarboxylic acids or dicarboxylic acid derivatives and aromatic diamines in the dipolar aprotic solvent. Examples of carboxylic acid components are terephthalic acid, 4,4'-biphenyldicarboxylic acid, 4,4'-diphenyl ether dicarboxylic acid, 4,4'-diphenyl sulfone dicarboxylic acid or 2,6-naphthalenedicarboxylic acid. Suitable diamine components are p-phenylenediamine, 3,3,'-dimethoxybenzidine, 3,3'-dichlorobenzidine, 3,3'-dimethylbenzidine, 4,4'-diaminodiphenylmethane, 2,2-bis-(4-aminophenyl)propane or 1,4-bis(4-aminophenoxy)benzene.

Particular importance is attached to membranes of those polyaramids which, in addition to a carboxylic acid component, contain different diamines as monomers. Thus, polyaramids have proved to be useful which are made up of terephthalic acid, p-phenylenediamine, 1,4-bis(4-aminophenoxy)benzene and 3,3'-dimethylbenzidine. The amines can be randomly distributed in the polymers, but the polyamides can also have the structure of block copolymers.

The mean molecular weight of the polyaramids can extend over a broad range. Usually, it is 5,000 to 200,000. Preference is given to polyaramids having a molar mass of 10,000 to 50,000.

To produce the membranes of the invention, a process has proved to be useful which is described in German Patent Application P 38 02 030. The membranes disclosed here consist of a copolyamide which is made up of three different diamines and one dicarboxylic acid. A solution of this copolyamide in an aprotic polar solvent of the amide type, e.g. N-methyl-2-pyrrolidone, is spread out as a liquid layer on a planar support. This liquid layer is introduced into the precipitant liquid, preferably water, which is miscible with the solvent of the solution, but the polymer precipitates out as a membrane. The precipitant liquid is allowed to act on the precipitated membrane until the solvent is completely replaced by the precipitant liquid. If necessary, the membrane can be further subjected to a heat treatment. The membrane is then dried, optionally after a prior treatment with glycerol.

The membranes produced by the above-described process are integrally asymmetric and are known in principle to those skilled in the art. The membranes have a very thin separation layer, whose thickness is 0.05 to 5 $\mu$, and a porous support structure. The thickness of the membrane consisting of separation layer and support structure can be 10 to 400 $\mu$, and is preferably in the range from 50 to 200 $\mu$.

The shape of the membrane can be selected as desired. It can be constructed as a disk, and, particularly, as a hollow fiber or capillary, but can also have any other shape suitable for the intended use. The critical factor is achieving a stability as high as possible and, furthermore, the highest possible surface area per unit volume to achieve a satisfactory throughput.

It is advisable to pretreat the membrane prior to use. In the simplest case, it is immersed into the solution to be separated. However, other conditioning processes are also possible. The membrane impregnated with glycerol for storage purposes is first washed with water and then left for 10 minutes in water at 80° to 100° C. The water is then replaced, e.g., by i-propanol, by layering the membrane in i-propanol and repeatedly replacing the alcohol. The i-propanol is then in the same manner replaced by the hydroformylation reaction mixture in which the organometallic complex compounds to be separated off and their ligands are dissolved.

To achieve an optimum separation efficiency, it has further proved to be useful to let the membrane run in under operating conditions for a certain time, i.e. to carry out the membrane filtration using the hydroformylation reaction mixture, but to recombine the resulting retentates and permeates and to recycle them to the hydroformylation reaction mixture upstream of the membrane filtration. As a result of this so-called pressure conditioning, further membrane pores close, as a result of which the separation efficiency of the membrane increases. The type and method of membrane conditioning determine the operating conditions to be maintained in the process according to the invention.

In the following examples, there are described several preferred embodiments to illustrate the invention. However, it is to be understood that the invention is not intended to be limited to the specific embodiments.

EXAMPLES

The production of a membrane of the type which can be used in the process according to the invention is described below.

Membrane Production

The polyaramid was prepared by condensation of
97–99 mol % of terephthaloyl dichloride
25 mol % of p-phenylenediamine
25 mol % of 1,4-bis(4-aminophenoxy)benzene
50 mol % of 3,3'-dimethylbenzidine
in N-methylpyrrolidone as solvent. Terephthaloyl dichloride was used in an amount such that the polyaramid had a Staudinger index of 200 to 300 ml/g. The amount of solvent was such that a solution containing about 7% by weight of polycondensate was formed. After the condensation had been carried out, the hydrogen chloride loosely bound to the solvent was neutralized by addition of 100 mol % CaO. 5% by weight (based on the polymer solution) of anhydrous calcium chloride were then dissolved, with stirring, in the reaction mixture. The solution was gently heated, filtered and degassed. It was used directly for membrane production.

It is possible to produce the membrane support-free or on a polyester fleece as support. Production of a support-free membrane is described below. The slightly heated polyaramid solution was drawn out with a blade on a glass plate to form a uniform film of about 150 $\mu$ and immersed in a waterbath of 2° C. After about 20 minutes, the membrane was pulled off from the glass plate and was placed for 5 minutes in water at 100° C. The membrane was then placed in i-propanol to replace the pore liquid water with alcohol. The membrane was then washed with toluene, and after this treatment, it was suitable for carrying out the separations. In all operations, care had to be taken to ensure that the membrane does not dry out.

Examples 2–6 and Comparison Examples 1, 7 and 8

Hydroformylation of dicyclopentadiene (DCP) using catalyst systems which comprise rhodium and various ammonium salts of triphenylphosphinetrisulfonate (TPPTS):

a) Preparation of the distearylammonium salt of TPPTS 253 g of an Na-TPPTS solution were introduced into a stirred flask under nitrogen and heated to 65° C. A solution of 250.3 g of distearylamine in 595 g of toluene was then added. In the course of 60 minutes, 90 ml of 20% strength sulfuric acid were added with stirring until a pH of 2.6 was attained, and the mixture was allowed to react further for 2.5 hours. 170 g of isopropanol were added for improved phase separation. After 15 minutes, 1037.5 g of an organic phase which contained the distearylammonium salt of TPPTS containing 0.33 mol of TPPTS per mol of amine were separated off. The organic phase contained 126 mmol of phosphorus(III)/kg.

Other ammonium salts of TPPTS (Examples 2–7 and Comparison Experiment 1) were prepared in a similar manner to the above instructions. The Jeffamines used in Example 3 used in Example 3 and the Comparison Examples 7 and 8 were commercial products of the Texaco Chemical Corporation and have the following structure:

Jeffamine M 600: (Molar mass = 600 g/mol)

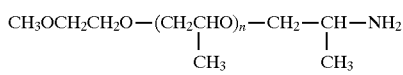

Jeffamine D 2000: (molar mass = 2000 g/mol)

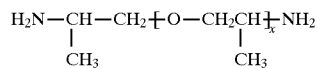

Jeffamine T 3000: (Molar mass = 3000 g/mol)

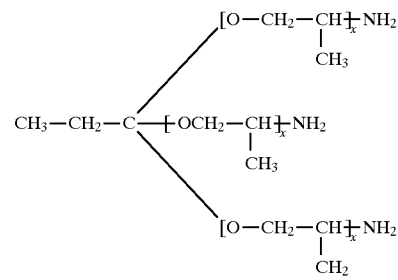

b) Batchwise hydroformylation of dicyclopentadiene, using the distearylammonium salt of TPPTS.

A 2.15 liter stirred autoclave was flushed with nitrogen and 212.8 g of the ligand solution from a) and 0.29 mmol of rhodium in the form of a 2-ethylhexanoate salt were dissolved (60 ppm by weight of Rh; P/Rh ratio: 100) in a glass vessel with nitrogen blanketing and 500 g of toluene were transferred under nitrogen into the autoclave. A pressure of 27 MPa was then established by feeding synthesis gas, with stirring. After a reaction temperature of 130° C. was achieved, preforming was carried out for two hours. 500 g of dicyclopentadiene were then pumped into the autoclave over the course of 1 hour. By cooling with an air fan, the temperature of 130° C. was maintained. After the completion of the dicyclo-pentadiene feed, the mixture was allowed to react for another 3 hours. The autoclave was then cooled to room temperatur and depressurized. The autoclave contents were then transferred by the residual pressure into a 2 liter three-neck flask equipped with an immersed branched stub and weighed. The dicyclopentadiene conversion rate was calculated from the increase in weight.

The hydroformylation of the dicyclopentadiene using the ammonium salts of TPPTS according to Example 3–6 and the Comparison Experiments, 1, 7 and 8 was performed in a similar manner. The results obtained are summarized in Table 1.

c) Single-stage membrane filtration

The particular above reactive product from b) was applied to a laboratory membrane filter unit wherein the membrane used was a polyaramid membrane from Hoechst AG (UF- PA(PET 100)). The membrane was first heated for 10 minutes at 80° C. in water and the membrane was then overflowed with 200 l/h using a circulation pump and a pressure of 1 MPa was established. At an operation temperature of 40° C., the amount of hydroformylation product reported in Table 1 passed through the membrane as permeate. The content of catalyst constituents was determined in the permeate, from which the retention values reported in Table 1 were obtained, based on the hydroformylation reaction mixture used.

It can be seen from Table 1 that only if a molar mass ratio [molar mass (ligand): molar mass (aldehyde)]=9–30 was maintained, were not only excellent selectivities obtained in the hydroformylation but outstanding retention values were also obtained in the membrane separation.

Example 9

A 5 liter stirred autoclave having an immersed branch stub for gas inlet and take off of products and a gas outlet valve was carefully flushed with nitrogen. 872 g of a toluene solution of the distearylammonium salt of TPPTS having a phosphorus(III) content of 138 mmol/kg and 120 mg of rhodium in the form of rhodium 2-ethyl-hexanoate were transferred into the autoclave by nitrogen overpressure from a reservoir.

The catalyst was then preformed for 2 hours at 27 MPa and 125° C. Then, in the course of 1 hour, 1,500 g of propylene were pumped in from a reservoir via the immersed tube (80 ppm of Rh, based on propylene; molar P: Rh ratio =100). The heat of reaction was removed via cooling coils in the reactor. The mixture was allowed to react further for 1 more hour and was allowed to cool. The autoclave was depressurized, and the mixture was transferred into a 3-neck flask using Schlenk fittings and weighed (3028 kg). The conversion rate was 95%, and the n/i ratio was 63/37.

The reaction product was then transferred into a laboratory membrane unit and filtered in 2 stages. The transmembrane pressure was 1.5 MPa. A UF-PA5 (PET 100) membrane from Hoechst AG was used. The retention values and flow rates reported in Table 2 were achieved.

The retentates of the 1st and 2nd stages were then recycled and again reacted with propylene in the autoclave. The very low losses of Rh and phosphorus(III) were compensated for as appropriate by addition of rhodium 2-ethylhexanoate and/or a solution of the distearylammonium salt of TPPTS. The supplementation was made to the permeate of the 1st stage.

The catalyst was recirculated in total 10 times without the conversion rate (90–95%), the selectivity (n/i ratio 63/37) or the retention values (see Table 2) changing significantly. In the values for the flow rate reported in Table 2, the first value was the initial value in the respective membrane filtration stage, whereas the second value characterized the equilibrium state.

Table 2 shows that, on reuse, the flow rate, owing to an accumulating concentration of thick oils, initially decreased, but stabilized at the lower level, i.e. that the thick oils also permeated and thus a separation of catalyst constituents and thick oil was possible.

Table 2 further shows that by the process of the invention, for the first time, metal complexes and excess ligands can be excellently separated off from the products, including thick oil, and recirculated.

TABLE 1

| Example | Amine in the ammonium salt of TPPTS | Molar mass M1 of the ammonium salt of TPPTS [g/mol] | Molar mass ratio M1 / M(TCD-dial)* | Hydroformylation Conversion rate [%] | Hydroformylation Selectivity dialdehyde/monoenal | Permeate quantity [% of initial amount] | Flow rate [l/m²h] | Retention [%] of initial amount Rh | Retention [%] of initial amount [P] | Retention [%] of initial amount [N] |
|---|---|---|---|---|---|---|---|---|---|---|
| 1(V) | Triisooctyl-amine | 1563.5 | 8.1 | 99.9 | 99/1 | 15 | 64 | 89.3 | 69.8 | 16.5 |
| 2 | Distearyl-amine | 2068.47 | 10.8 | 99.4 | 97/3 | 66 | 61 | 97.5 | 96.1 | 78.3 |
| 3 | Jeffamine M600 | 2302.47 | 12.0 | 98.8 | | 23 | 9 | 99.7 | 98.7 | 63.9 |
| 4 | Tricetyl-amine | 2573.43 | 13.4 | 98.7 | 96/4 | 22 | 44 | 95.0 | 90.0 | 73.3 |
| 5 | Tri-n-octa-decylamine | 2825.91 | 14.7 | 98.5 | 91/9 | 53 | 49 | 93.0 | 87.0 | 88.7 |
| 6 | Tridocosyl-amine | 3330.87 | 17.3 | 99.7 | 90/10 | 48.8 | 29 | 96.5 | 94.7 | 81.9 |
| 7(V) | Jeffamine D2000 | 6502.47 | 33.8 | 98.1 | 69/31 | 29 | 22 | 99.5 | 89.4 | 93.9 |
| 8(V) | Jeffamine T300 | 9502.47 | 49.4 | 98.4 | 63/37 | 56 | 31 | 99.7 | 97.7 | 91.4 |

*M(TCD-dial) = 192.26 g/mol

TABLE 2

Membrane separation and recycling of an Rh-catalyst system containing the distearylammonium salt of TPPTS as ligand in the hydroformylation of propylene.

| Hydroformylation | | | Membrane filtration | | | | | |
|---|---|---|---|---|---|---|---|---|
| | | | Permeate quantity [% of initial amount] | | Retention [% of initial amount] | | Flow rate [l/m²/h] | |
| Reaction time [h] | Temperature [°C.] | Recirculation | 1st stage | 2nd stage | Rh | P [total] | 1st stage | 2nd stage |
| 2   | 125 | 0  | 87 | 86 | 95.96 | 89.3 | 103–10 | 136–51 |
| 2   | 125 | 1  | 85 | 94 | 99.23 | 92.7 | 97–16  | 115–40 |
| 2   | 125 | 2  | 85 | 96 | 99.71 | 99.3 | 92–47  | 82–29  |
| 2   | 125 | 3  | 88 | 93 | 98.85 | 99.2 | 82–15  | 75–24  |
| 2   | 125 | 4  | 84 | 94 | 99.30 | 99.4 | 76–17  | 68–28  |
| 2.3 | 125 | 5  | 82 | 90 | 99.57 | 98.9 | 72–17  | 56–15  |
| 2.5 | 127 | 6  | 83 | 95 | 98.61 | 99.0 | 67–13  | 66–18  |
| 2   | 128 | 7  | 84 | 93 | 99.52 | 97.2 | 67–12  | 89–30  |
| 2   | 126 | 8  | 83 | 94 | 99.09 | 96.7 | 63–10  | 74–16  |
| 2   | 128 | 9  | 83 | 94 | 99.07 | 97.6 | 58–10  | 76–22  |
| 2.5 | 125 | 10 | 81 | 93 | 98.80 | 98.2 | 56–12  | 62–21  |

Various modifications of the process of the invention may be made without departing from the spirit or scope thereof and it is to be understood that the invention is intended to be limited only as defined in the appended claims.

What I claim is:

1. A process for preparing aldehydes comprising hydroformylating olefinically unsaturated compounds with hydrogen and carbon monoxide in a homogeneous phase in the presence of a catalyst system comprising organometallic complex compounds and ligands of these complex compounds in molar excess, and separating off the catalyst system from the hydroformylation reaction mixture by pressure filtration on an integrally asymmetric, porous semipermeable membrane of an aromatic polyamide, in which the molar mass ratio of the ligands present in excess to the aldehydes prepared is 9–30 with the ligands present in excess not being alkylammonium or arylammonium salts of sulfonated, carboxylated or phosphonated aromatic diphosphines.

2. The process of claim 1, wherein the metal of the organometallic complex compounds is an element selected from the group consisting of metals of groups IVA, VA, VIA, VIIA, VIIIA and IB of the Periodic Table of the Elements.

3. The process of claim 2, wherein the metal is selected from the group consisting of manganese, iron, cobalt, nickel, palladium, platinum, ruthenium, rhodium and iridium.

4. The process of claim 1, wherein the ligands present in excess are monodentate ligands and the molar ratio of monodentate ligands to organometallic complex compound in the hydroformylation is at least 50.

5. The process of claim 1, wherein the ligands present in excess are selected from the group consisting of sulfonated pyridines, quinolines, 2,2'-bipyridines, porphyrins, pyridylphosphines, quinine, glyoxime, sulfonated phosphites and alkyl- and aryl-substituted acetylacetonates, salicylates and mandelates.

6. The process of claim 1, wherein the olefin is reacted with carbon monoxide and hydrogen at a temperature of 100 to 140° C., and at a pressure of 0.5 to 27 MPa.

7. The process of claim 1, wherein, for the hydroformylation, olefinically unsaturated compounds of 2 to 30 carbon atoms, which can have one or more double bonds, are reacted.

8. The process of claim 1, wherein it is carried out in the presence of an organic solvent.

9. The process of claim 1, wherein, in the hydroformylation reaction mixture used for membrane filtration, the concentration of the complex compound ligands present in excess is 2.5–25, % by weight, based on the reaction mixture used for the membrane filtration.

10. The process of claim 1, wherein the concentration of the organometallic complex compounds in the hydroformylation reaction mixture used for the membrane filtration is 2–400 ppm by weight, based on the reaction mixture used for the membrane filtration.

11. The process of claim 1, wherein the membrane filtration is performed on a polyaramid membrane at a pressure of 0.1 to 15 MPa, and is carried out in a single stage or in multiple stages.

12. The process of claim 11 carried out in two stages.

13. The process of claim 1, wherein the membrane filtration is carried out with series-connected separation stages.

14. The process of claim 1, wherein the total amount of retentate of the membrane filtration is 8–90% based on the hydroformylation reaction mixture used, and the concentration of the separated ligands of the complex compounds in the retentate is at least three times as high as in the hydroformylation reaction mixture used for the membrane filtration.

15. The process of claim 1, wherein, in the two-stage membrane filtration, the ratio of the amount of retentate of the 1st filtration stage to the amount of retentate of the 2nd stage is about 1:1.

16. The process of claim 1, wherein the membrane filtration separation stage retentates containing the catalyst system are recycled back to the hydroformylation, with or without supplementary addition of the metal and/or of the organometallic complex compound and of the ligands of these complex compounds.

17. The process of claim 16, wherein, in the case of a two-stage membrane filtration procedure, the supplementary addition of the metal and/or of the organometallic complex compounds and of the ligands of these complex compounds is even made to the permeate of the 1st filtration stage prior to its feed to the 2nd filtration stage.

18. The process of claim 1, wherein the solvent is separated off from the combined permeates of the membrane filtration separation stages by distillation, recycled upstream of the membrane filtration and added to the hydroformylation reaction mixture upstream of the membrane filtration.

* * * * *